United States Patent [19]
Blackwell et al.

[11] Patent Number: 4,590,292
[45] Date of Patent: May 20, 1986

[54] PROCESS FOR THE MANUFACTURE OF CYCLOPROPYLAMINE

[75] Inventors: Joseph T. Blackwell, Denham Springs; Harold L. Daughety, Baton Rouge; Henry C. Grace, Baton Rouge; Ward H. Oliver, Baton Rouge, all of La.

[73] Assignee: Ciba-Geigy Corporation, Ardsley, N.Y.

[21] Appl. No.: 742,680

[22] Filed: Jun. 10, 1985

[51] Int. Cl.$^4$ ............................................ C07C 85/153
[52] U.S. Cl. ................................... 560/124; 562/602; 564/1; 564/137
[58] Field of Search ............... 562/602; 560/124; 564/137, 134, 1

[56] References Cited

U.S. PATENT DOCUMENTS

| | | | |
|---|---|---|---|
| 2,449,993 | 9/1948 | Gresham | 562/602 |
| 2,839,576 | 6/1958 | Phillips | 562/602 |
| 3,010,971 | 11/1961 | Kaiser | 560/124 |
| 3,077,496 | 2/1963 | Julia | 560/124 |
| 3,123,629 | 3/1964 | Julia | 560/124 |
| 3,294,833 | 12/1966 | Phillips | 560/124 |
| 3,417,114 | 12/1968 | Kuceski | 564/134 |
| 3,538,159 | 11/1970 | Duffy | 564/137 |
| 3,711,549 | 1/1973 | Phillips | 564/134 |
| 4,265,819 | 5/1981 | Lantzsch | 560/124 |
| 4,520,209 | 5/1985 | Schwarze | 560/124 |

OTHER PUBLICATIONS

March, "Advanced Organic Chemistry: Reactions, Mechanisms, and Structure," pp. 338 and 339 (1968).

Primary Examiner—Michael L. Shippen
Attorney, Agent, or Firm—Karl F. Jorda

[57] ABSTRACT

A modified novel process for preparing cyclopropylamine from γ-butyrolactone is described. The γ-butyrolactone ring is cleaved with a hydrohalide in the presence of a novel catalyst comprising an aqueous sulfuric acid solution. The 4-chlorobutyric acid, thus formed is converted into a hindered chlorobutyrate ester. The hindered ester based on secondary and tertiary alkanols of eight or less carbon atoms, is cyclized to form the hindered cyclopropanecarboxylate ester by a novel reaction medium consisting of solid caustic in a water-immiscible solvent and a phase transfer catalyst. The hindered cyclopropanecarboxylate ester is ammoniated to form cyclopropanecarboxamide by a novel catalyst comprising an alkali metal salt of a polyol having hydroxy groups on adjacent carbons. The carboxamide formed in substantially quantitative yields is converted to cyclopropylamine by a modified Hofmann reaction utilizing continuous degradation of the intermediate with simultaneous distillation.

14 Claims, No Drawings

PROCESS FOR THE MANUFACTURE OF CYCLOPROPYLAMINE

FIELD OF THE INVENTION

This invention relates to the manufacture of cyclopropylamine and more particularly to a novel economic process for its manufacture from gamma-butyrolactone and refinements including novel intermediate steps.

BACKGROUND OF THE INVENTION

Cyclopropylamine (CAS) [765-30-0] is an important intermediate in the synthesis of many important organic compounds. For example, cyclopropylamine is a useful intermediate for the synthesis of 6-cyclopropylamino-2-chloro-s-triazine herbicides. It is also an intermediate for the synthesis of cyromazine; N-cyclopropyl-1,3,5-triazine-2,4,6-triamine; an ectoparasiticide marketed by Ciba-Geigy and formulated as Vetrazine®, Larvadex® and Trigard®.

Previously, the route to cyclopropylamine was via cyclopropane carbonitrile. This is hydrolyzed to cyclopropane carboxamide in aqueous acid. This is then converted to cyclopropylamine by the Hofmann reaction in alkali hypochlorite and alkali hydroxide solution.

Recently, U.S. Pat. No. 3,711,549 disclosed converting gamma-butyrolactone to cyclopropylamine by cleaving gamma-butyrolactone in the presence of zinc chloride at 120° C. at 300 psig. The resultant 4-chlorobutyric acid is then esterified with methanol to form 4-chlorobutyrate methyl ester. This ester is then cyclized to form the cyclopropanecarboxylic acid methyl ester. This cyclization reaction requires pre-esterification of the acid as the cyclization conditions would otherwise merely result in conjugation polymerization of the butyric acid moiety or ring closure to reform γ-butyro-lactone. According to this patent, the resulting cyclopropane carboxylate ester, after closing the cyclopropane ring, is then amidated with gaseous ammonia under anhydrous conditions in the presence of toluene and sodium methoxide to form cyclopropanecarboxamide. While 90% conversion of the ester is reported, this figure includes repeated recycling of the unreacted cyclopropane carboxylate methyl or ethyl ester in the toluene solution.

This reaction requires toluene as the medium for the sodium methoxide reaction, as low overall yields of amide are reported when toluene is not used. The cyclopropane carboxamide is then converted to cyclopropylamine by the Hofmann reaction using aqueous alkali hypochlorite and alkali hydroxide for the hydrolysis. The chemistry of the Hofmann reaction has been summarized in "Organic Reactions", Vol. 3, 267–306 (1946).

This general reaction scheme can be represented by the diagram as follows:

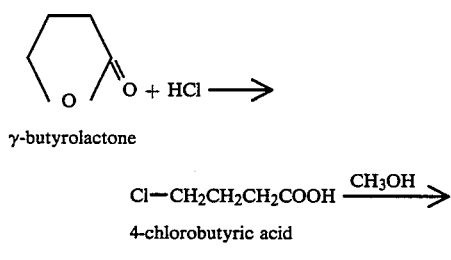

γ-butyrolactone

Cl—CH$_2$CH$_2$CH$_2$COOH $\xrightarrow{\text{CH}_3\text{OH}}$ 4-chlorobutyric acid

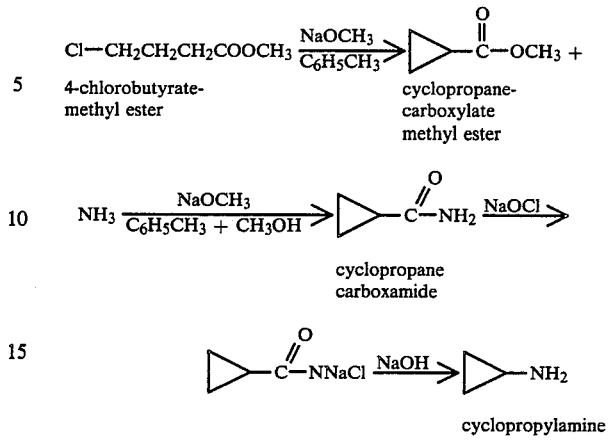

The above reaction scheme, while starting with an inexpensive acetylene chemical, γ-butyrolactone, involves the use of sodium metal in the manufacture of the fresh sodium methoxide needed for the ring closure. In plant scale manufacture, this presents considerable problems of safety in handling and the economics and overall yields on such a scale are also less than desirable.

There are several additional references in the literature to various chemical routes for the preparation of cyclopropylamine on a laboratory scale. Among these are: M. J. Schlatter, Journal of the American Chemical Society, 63, 1733 (1941); G. D. Jones, Journal of Organic Chemistry, 9, 484 (1944); W. D. Emmons, Journal of the American Chemical Society, 79, 6522 (1957). While convenient for laboratory use, the procedures in these cited articles are not suitable for large-scale commercial use due to low yields and/or use of expensive reagents.

THE INVENTION

In the process of the present invention, the overall scheme from γ-butyrolactone, cleavage by reaction of hydrohalide, esterification of the halobutyric acid, ring-closure of the carboxylate ester and subsequent amidation and conversion to cyclopropylamine is followed, but with special modifications of the reaction conditions, special reactants, protective moieties and catalysts to provide a novel overall scheme, with economic yields.

The novel reaction sequence of this invention to form cyclopropylamine from γ-butyrolactone consists of five primary reaction sequences as follows:

(1) Gamma-butyrolactone (BLT) cleavage by a hydrohalide which is promoted by a novel inexpensive catalyst;
(2) Esterification of the 4-chlorobutyric acid (CBA) cleavage product, with secondary or tertiary alcohols to form 4-chlorobutyrate esters (CBE) which promote completion of the subsequent cyclization;
(3) Cyclizing the butyrate ester (CBE) in the presence of a novel basic reactant and catalyst system, which eliminates the requirement for dangerous and expensive sodium methoxide, to form cyclopropane carboxylate esters (CPE);
(4) Amidating the cyclized ester (CPE) with gaseous or liquid ammonia by the use of a novel alkali metal oxide alkanediol salt catalyst directly prepared from the polyol with alkali hydroxide; and (5) Reacting the resulting cyclopropane carboxamide (CPAM) with alkali hypochlorite to form a chlorinated intermediate which is subsequently converted to cyclopropylamine in a novel, continuous reaction process with significant cost and safety advantages.

NOVEL CATALYTIC BLT CLEAVING

As mentioned above, 4-chlorobutyric acid (CBA) is the intermediate produced in the first step of the five step process (above) for converting gamma-butyrolactone (BLT) to cyclopropylamine (CPA).

In the third step of this process, an ester of CBA is cyclized to the cyclopropane analog. Attempts were made to synthesize the 4-chloro-butyrate ester (CBE) directly from butyrolactone, hydrogen chloride and the appropriate alcohol. It was found that the direct approach would not work because, (a) low reaction temperatures (30°–35° C.) had to be used to prevent the formation of alkyl chlorides from the alcohol and the hydrogen chloride and as a result, reaction times exceeded several days;

(b) the large excesses of hydrogen chloride (200–300% of theory) complicated the workup of the reaction mass.

It was thus proven that it was more efficient to form CBA from BLT and then to esterify the CBA to CBE by traditional methods. BLT cleaves directly with HCl at elevated temperatures and pressure and no solvent to form CBA. However, an appropriate catalyst will increase the reaction rate. The CBA produced can then be directly esterified to CBE without a purification step.

In this cleaving step, stoichiometry and pressure are interrelated, as at a given temperature, the pressure will be dependent on the excess amount of hydrogen chloride charged.

Pressurizing the reaction has the effect of increasing the amount of hydrogen chloride dissolved in the reactants and products and thus available for reaction. At 70–80 psi, the hydrogen chloride is present in 10–15% excess. This pressure can be handled conveniently in general glass-lined plant equipment. Higher pressures, e.g. up to 300 psig, which accelerate the reaction times, require reinforced equipment which increases the equipment costs.

Reaction temperature studies indicate that the optimum temperature for the ring cleavage is in the range 70°–75° C. While the reaction will proceed at lower temperatures, the reaction time is increased. At higher than 75° C., the reaction begins to reverse, i.e. CBA breaks down to BLT and hydrogen chloride. While at 120° C., the forward reaction still predominates, the conversion of BLT is appreciably reduced. It is apparent that another temperature and pressure dependent equilibrium is involved.

Previous reports on this cleavage reaction, U.S. Pat. No. 3,711,549, where zinc chloride was used as the catalyst, and Oelschlager et al Archiv du Pharmazie, 294, 488 (1961) where no catalyst was used, resulted in, at best, 85% yield of CBA with the formation of large amounts of impurities. However, we have discovered that when gamma-butyrolactone was reacted with about 10% molar excess of HCl, with 5–10 wt% of a 35–40% solution of $H_2SO_4$ in water as catalyst, a 95% yield of crude CBA was isolated suitable for esterification in both laboratory and large scale production runs. This catalyst is much less expensive than zinc chloride and avoids difficult environment strictures. In lieu of sulfuric acid, phosphoric acid or methanesulfonic acid can be used.

ESTERIFICATION

As mentioned above, in order to cyclize the 4-chlorobutyric acid at the third stage of the main reaction sequence, it is necessary to protect the butyrate moiety by esterification. However, due to the tendency for the esterification reaction to be in equilibrium with hydrolysis, it is useful to catalyze the reaction toward reaction completion by using a water-immiscible solvent and removing the water formed in the esterification by azeotropic distillation. Toluene is the preferred water-immiscible reaction solvent but benzene and xylene will also serve the reaction.

The choice of the alcohol moiety is determined by the stability of the CBE during the conditions of the novel ring closure in the next stage of the reaction.

It was found that primary esters gave unsatisfactory results. The esters of the tertiary alcohol gave excellent results, 95–100% ring closure, but the CBE esters of these alcohols were more difficult to prepare. The tertiary-butyl ester provided nominally 100% yield. The secondary alcohol CBE esters gave satisfactory results at temperatures of about 20°–60° C. The isopropyl and 2-butyl esters of 4-chlorobutyric acid cyclized to in-hand yields of 93 to 98%.

Thus, the second stage of the reaction scheme comprises esterification of the 4-chlorobutyric acid with a secondary or tertiary alcohol in toluene in the presence of an acid.

CATALYTIC CYCYLIZATION OF CBE TO CPE

Esters of cyclopropanecarboxylic acid, usually methyl or ethyl, have been prepared in useful yields from the corresponding ester of 4-chlorobutyric acid when treated with the sodium alkoxide (U.S. Pat. No. 3,711,549). Sodium alkoxides are generally prepared by the action of sodium metal on the corresponding alcohol. Sodium metal is relatively expensive and presents hazards in handling the large quantities of the material needed for commercial production. Absolute anhydrous conditions are required to prevent explosive hazards.

Several sodium alkoxides of high boiling alcohols have been prepared by treating such alcohols with sodium hydroxide and removing the formed water by distillation as illustrated by the following equation:

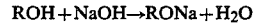

$$ROH + NaOH \rightarrow RONa + H_2O$$

However, these alkoxides gave poor results when used to convert esters of 4-chlorobutyric acid to the cyclopropane analogs.

It is known that 4-chlorobutyronitrile ($ClCH_2CH_2CH_2CN$) can be converted to cyclopropanecarbonitrile in good yield using solid sodium hydroxide, a solvent, and a phase transfer catalyst (PTC). However, when the same conditions were used with the methyl ester of chlorobutyric acid (U.S. Pat. No. 3,711,549), little cyclization was obtained. The major reaction was hydrolysis of the ester.

As mentioned above in the second section on ester formation, it is known that the esters of secondary and tertiary alcohols are hydrolyzed with increasing difficulty compared to primary esters. One of the inventive aspects of this step is the discovery of conditions and catalysts whereby secondary esters of CBA are converted by solid caustic to the CPE in good yield with little hydrolysis. The reaction may be represented by the following equation:

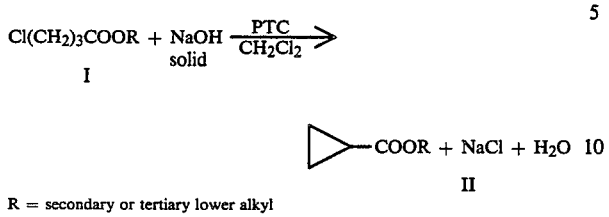

R = secondary or tertiary lower alkyl

The effect of different primary, secondary and tertiary esters on the above reaction was investigated. Table I shows these effects:

| R= | T(°C.) | Yield of II |
|---|---|---|
| n-butyl | 35° | 53% |
| isopropyl | 55° (reflux) | 93% |
| 2-butyl | 55° (reflux) | 93+% |
| tert-butyl | 55° (reflux) | 100% |

The above results show that primary esters give unsatisfactory yields. Tertiary esters give excellent yields but the tertiary butyl 4-chlorobutyric ester is more difficult to prepare. Secondary esters provide the most satisfactory yields under these conditions and are preferred, with the 2-butyl being most cost-efficient.

It is preferred to add the secondary ester CBE to a mixture of a solvent, NaOH and the PTC. The rate of addition is adjusted to keep the reaction rate within the capabilities of the reactor cooling system to handle the heat evolved.

The reaction times for reaction completion, as determined by gas chromotography, were tested in the lab and it was found that in the range 30°–40° C., 3 to 6 hours was satisfactory. This time frame would permit heat removal in large scale reaction equipment. However, it is preferred to maintain the reaction at about 30°–55° C. Under these preferred conditions, the reaction was completed within several hours under plant conditions. The choice of solvent is preferably a non-hydrolyzing solvent that permits temperature control within the range 30°–40° C. Excellent yields were obtained with methylene chloride and methyl t-butyl ether. A solvent is not necessary as good yields (95%) were obtained without a solvent but a solvent made handling safer and more convenient. Hexane, cyclohexane, toluene and similar solvents can also be used but methylene chloride and methyl-t-butyl ether are the preferred solvents.

The cyclization of CBE to CPE is promoted by phase transfer catalysts (PTC), usually a quaternary ammonium chloride salt. Tributyl methylammonium chloride is among the best for this reaction but trimethyl- and triethylbenzylammonium chlorides as well as tricaprylmethyl ammonium chloride have been found satisfactory. The tetrabutyl-ammonium bromide was found to be effective but less satisfactory.

In this reaction, cyclopropane carboxylic esters are obtained in high yield under conditions amenable to large scale production and use of readily-available materials. Such products are readily converted to derivatives of cyclopropane carboxylic acid and then to products where the cyclopropane moiety is desirable. Among such products are intermediates and ultimate agricultural and pharmaceutical chemicals.

The novelty of this invention is the discovery that secondary esters of 4-chlorobutyric acid can be converted to the corresponding cyclopropane derivatives in excellent yields using alkali metal hydroxides. The prior art teaches the use of primary alcohol esters and their conversion by the more expensive and hazardous sodium alkoxides (sodium methoxide).

The prior art shows that an attempt had been made to convert the 4-chlorobutyrate ethyl ester to the cyclopropane carboxylate ester using 50% aqueous KOH in 400% excess in the presence of a large volume of toluene and a phase transfer catalyst. Gas chromatography on the solution of the product indicated a 91% yield. However, no actual yields on recovery of the product from the solution were reported, as compared to the other esters in the reported series. (R. Lantzsch *Synthesis*, 955 (1982) Georg Theime Verlage, Stuttgart-New York.) The novel use of solid alkali hydroxide in only 50% excess for the cyclization of 4-chlorobutyrate esters to the cyclopropanecarboxylate esters in 95+% yields in a non-hydrolyzing solvent is a novel inventive feature of this stage of the present invention.

AMIDATION OF CYCLOPROPANECARBOXYLATE ESTERS

This stage is the most critical of all the stages of the overall scheme of the main invention. This step according to the prior art (U.S. Pat. No. 3,711,549) is the most critical of the entire process, not only because the conversion to the desired product is lower (thus limiting the overall yield) but because the amide product is sensitive to alkaline hydrolysis. By the procedures of said prior art, the stated best recovered yields are about 88%.

Our invention, involved in this stage of the overall reaction, is a novel catalyst system for improving the efficiency of amidation or ammonolysis of organic esters to form amides:

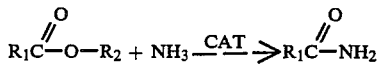

where $R_1$ is cyclopropyl, cyclopropyl-substituted on the propyl ring, cyclopropyl alkyl, and cycloalkyl to six carbons and $R_2$ is an alkyl group from methyl through $C_8$ of straight or branched alkyl chains.

The catalyst is exemplified by the formula:

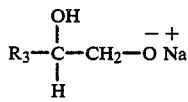

where $R_3$ is H—, $CH_3$—, $HOCH_2$—, $CH_3(CH_2)_x$—, and $HO(CH_2)_x$—, i.e. the sodium salt of a polyhydric alcohol with at least two hydroxy groups on adjacent carbons.

In the past, the texts and literature sources have taught the reaction of esters and ammonia to form amides. However, under mild reaction conditions, only inductively activated esters react rapidly. Even in these cases, most often the reaction is incomplete due to an additional equilibrium with the alcohol (regeneration of the ester). The larger and more hindering the alcohol, the more the equilibrium favors the ester. The ester is more stable and more difficultly amidated. For normal alkyl and cycloalkyl esters of alkyl and cycloalkyl carboxylic acids, the mild reaction conditions are of limited commercial use. Present commercial efforts have been directed to the use of high pressures and temperatures for extended reaction times.

Several prior art techniques have been employed to catalyze ester ammonolysis. The preferred catalysts, prior to this invention, were the alkali metal alkoxides of monohydric alcohols such as sodium methoxide. In general, methanol esters were useful but as shown in the above cited patent, the equilibrium limits the yield to about 85-88%. The alcohol and solvent stoichiometry are critical to operation of that process. Our tests have now shown that higher alcohol esters favor the ester over the amide in the reaction equilibrium so that very little of the desired reaction takes place. When the alkali metal alkoxides of higher primary alcohols are substituted for the sodium methoxide, they do not form the amides in useful amounts.

Attempts have been made to use ethylene glycol and related diols as catalysts to promote the amidation reaction of hindered alcohol esters. However, the reaction was so slow that very long times were needed to provide even incomplete conversion to the amides. Tests show that adding glycol alone to the CPE ester/ammonia reaction mass does not significantly improve the reaction rate.

Our invention is based on discovery that the reaction rate and conversion are highly dependent on the presence and amount of the sodium ethylene glycoxide or glyceroxide (below 0.2 mole catalyst/mole ester). When the sodium ethylene glycoxide is added to the ammonia/ester reaction mass of even the most hindered alcohol esters, the reaction to form the amide is rapid and generally is 100% complete.

The catalysts of this specific invention are easily prepared without the need for resorting to the use of alkali metals, i.e., sodium and potassium. These metals are extremely reactive and present explosive hazards when accidently exposed to water. Thus, if possible, such metals should be avoided for large scale plant operations.

Our catalysts are prepared by mixing an alkali metal hydroxide with an excess of the glycol or glycerol and vacuum distilling or otherwise removing the water as it forms, from the product. Sodium ethylene glycoxide is prepared as needed by vacuum distilling the water from a mixture of solid caustic (NaOH) and excess ethylene glycol in accordance with the following equation:

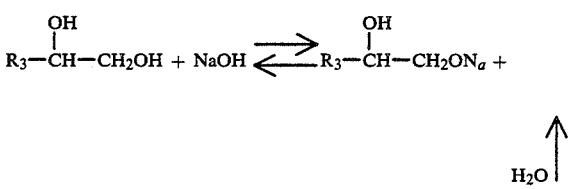

The preferred scheme of the novel overall reaction invention uses the novel 2-butyl cyclopropanecarboxylate, prepared as described for CPE above, stripped of water and low boiling compounds. This is reacted with technical grade ammonia in the presence of the sodium ethylene glycoxide catalyst.

In a typical batch, the ester is charged into a pressure reactor. The sodium ethylene glycoxide in ethylene glycol is then introduced. On a molar basis, for every mole of the ester charged, the minimum sodium ethylene glycoxide charge is 0.05 moles. However, for effective reaction rates, the catalyst level is at least about 0.1 and preferably about 0.2 moles. There is no upper catalyst limit beyond keeping the glycol level in the effluent as low as possible. Enough glycol is present in the catalyst (from the excess used in its preparation) to solubilize the sodium ethylene glycoxide as a homogeneous solution. This permits convenient handling during preparation of the catalyst and charging it to the reaction. The excess glycol can be reduced to keep the catalyst as a slurry but this offers little advantage.

Solvents including alcohols and aromatic hydrocarbons have been used in the reaction mass containing the sodium ethylene glycoxide catalyst but some tend to reduce the yield and all adversely affect the reactor throughput.

There is no restriction on the amount of ammonia charged. Total conversion requires a minimum of 1 mole/mole of ester. About 1.3 moles of ammonia favors the reaction. More or less ammonia can be used but at the cost of optimum raw material usage and reactor throughput.

The preferred reaction temperature is in the range 85°-115° C. because it provides the optimum reaction rate versus yield tradeoffs. Lower temperature seems to favor a slight increase in yield but at a sacrifice to reactor throughput, i.e., longer residence time. At about 140° C. there is evidence that the equilibrium may be shifting toward the ester and the yield is lower. A broad range within which this catalyzed reaction is operative is 25°-150° C. but the preferred range, as stated, is 85°-115° C. with 100° C. as the target or optimum.

After charging the ester and catalyst, the reactor is flushed with gaseous ammonia and the reactor is then sealed and heated to about 100° C. The pressure in the reactor at 100° C., with ethylene glycol as the catalyst solvent, is then maintained at 50-90 psi by adding ammonia as needed. This is well within the parameters of the usual commercial pressurized reactors.

Alternatively, all of the ammonia can be added before the reactor is sealed and heated as the reaction proceeds at autogenous pressures.

For the preferred system at 100° C., a minimum reaction time at 50-90 psi pressure for good yield is about one hour. In practice, the reactor is typically held 2-3 hours to assure total conversion. Holding the reaction mass for an extended time at 100° C. does not noticeably affect the yield, though it does affect throughput.

Thus, this reaction step comprises reacting a hindered ester of cyclopropanecarboxylic acid with ammonia in the presence of the alkali metal salt of a polyhydric alcohol of 2-5 carbon atoms, said polyhydric alcohol having at least two hydroxy groups on adjacent carbons, said reaction being promoted at temperatures in the range 25° to 140° C., preferably in the range 85°-115° C., optimally at about 100° C. and 50-90 psi pressure. The yields of cyclopropanecarboxamide by this reaction are above 90%, i.e., about 93-97%.

This ammonolysis process makes possible the ultimate production of cyclopropylamine with less expensive and less hazardous chemicals by successive steps wherein the cyclopropyl ring closure step uses caustic, not sodium methoxide and wherein the hydrolysis, which usually takes place during the ring closure, is minimized by the use of a secondary or tertiary alcohol for the cyclized ester, preferably the sec-butyl ester, i.e., a hindered ester. However, with the prior art catalysts, the resulting hindered cyclopropane esters could not be converted to cyclopropanecarboxamide. However, this step of amidation can be performed with the sodium or potassium salt of a short chain polyhydric alcohol having at least two hydroxy groups on adjacent carbons as catalyst. This amidation with sodium ethylene glycoxide (or glyceryloxide) makes possible the use of the hindered esters to perform the novel, quick, simple reaction that approaches and often achieves a 100% ester conversion.

Further, the use of hazardous sodium metal is not needed for preparing sodium ethylene glycoxide. Solid caustic, NaOH or KOH, is simply added to the glycol or glycerol or other diol and then stripped of the resulting water. Ethylene or propylene glycol or glycerin are particularly suitable.

CONVERSION OF CYCLOPROPANECARBOXAMIDE TO CYCLOPROPYLAMINE BY THE HOFMANN REACTION

The previously cited Gulf patent (U.S. Pat. No. 3,711,549) teaches the addition of an acidified aqueous solution of cyclopropane carboxamide to cold sodium hypochlorite solution, followed by addition of caustic to the cold reaction mass, then warming and controlling the temperature between 40° C. and 50° C. for a reaction period. The cyclopropylamine product is then isolated in a separate distillation step.

As the cited patent infers (the middle of column 6), the procedure discussed requires a high cooling capacity for the batch or semi-continuous operation in which the intermediate reaction mass is warmed to 40°-50° C. due to the large heat of reaction. The energy requirements for this cooling capacity are large and expensive at today's high utility rates. Moreover, the loss of cooling capability due to electrical outage or refrigeration compressor and/or pump problems during this critical step would pose a severe safety risk. The specified range of temperatures is just below the boiling point of the cyclopropylamine product (50° C.). If cooling is lost, and the temperature rises above 50° C., large volumes of CPA vapors are generated very quickly, which can lead to overpressurization of the reaction vessel. In the worst case situation, catastrophic failure of the vessel would lead to severe damage to equipment and/or injury to personnel.

The inventive improvement disclosed here eliminates these safety risks and the high energy costs associated with brine cooling to keep the reaction temperature below 50° C. This is accomplished by adding aqueous sodium hypochlorite containing a slight excess of caustic to a cold, aqueous slurry of cyclopropane carboxamide. The resultant solution of chlorinated intermediate is aged for about an hour to ensure reaction completion. The cold solution is then pumped slowly and continuously to the middle of a continuous distillation column containing, at startup, hot, boiling water. Aqueous caustic is fed into the stream of chlorinated intermediate solution at a point shortly before it enters the distillation column. Automatic instruments and controls, well known to those skilled in the art, are used to ensure that slightly in excess of two moles of caustic per mole of chlorinated intermediate are mixed into the stream. Under these conditions, the chlorinated intermediate in the presence of excess caustic enters the hot, continuous distillation column and decomposes very quickly and essentially quantitatively to the desired cyclopropylamine product. The low boiling CPA product distills overhead, is condensed, and collected in a receiver. The aqueous reaction solution, free of CPA and containing the salt and sodium carbonate byproducts, exits the system via the bottom of the distillation column. In essence, the heat of reaction which was removed by expensive refrigeration at some risk in the prior art, is now utilized to help drive the distillation and maintain reflux in the column. Risk of overpressurization is now minimal since the reaction mass is kept cold until it reaches the distillation column where it reacts quickly and cleanly. In case of upset conditions, risks are further minimized by the fact that only a relatively small portion of the reaction mass is in the hot zone at any given time and flow can be stopped easily until the problem is corrected.

CLEAVING THE LACTONE

Example 1—Lab Scale

A 750 ml Teflon-lined autoclave is charged with 344.4 g (4.0 moles) gamma-butyrolactone, 18 g water and 6.8 g sulfuric acid. The autoclave is sealed, and 163 g (4.47 moles) anhydrous hydrogen chloride is slowly charged to the batch. Temperature and pressure rise as the hydrogen chloride is charged; a reaction temperature of 70°-75° C. and a reaction pressure of 70-80 psi are maintained until analysis of the batch shows the reaction to be complete (24 hours). The reactor is then vented of excess pressure, and cooled. 551 g of crude CBA is obtained assaying 85.0% CBA. The yield of CBA, based on butyrolactone charged, is 95.5%.

Example 2—Pilot Plant Scale

A 50 gallon glass-lined autoclave is charged with 215 lb. (2.5 lbs.-moles) of gamma-butyrolactone, 11 lbs. water and 4.3 lbs. sulfuric acid. To this is slowly charged 105 lbs. of anhydrous hydrogen chloride. Temperature and pressure rise as the hydrogen chloride is charged; a reaction temperature of 65°-75° C. and a reaction pressure of 70-80 psi are maintained until analysis of the batch shows the reaction to be complete. The reactor is then cooled and excess pressure vented. The crude 4-chlorobutyric acid is then ready for further use. A CBA yield of 95.8% (assaying 92.1%) based on butyrolactone is obtained.

PREPARATION OF ESTER

EXAMPLE 3

To a one-liter 5-neck flask fitted with an agitator, distillation column and head, a Barrett trap and condenser, 122.6 g 4-chlorobutyric acid (CBA) in the form of crude CBA containing sulfuric acid, 111.2 g 2-butanol (SBA) and 100 ml toluene are charged. The batch is heated to reflux, returning the condensate through the Barrett trap as it forms. Heating is continued until water no longer separates in the trap; at this point the reaction is complete. The batch is cooled to 35°-40° C. and 100 g water and 10 1 g NaHCO$_3$ are charged. The batch is agitated for 15 minutes, then the agitator is stopped and the layers are allowed to separate. The lower aqueous layer is split off and discarded. The Barrett trap is removed from the reaction flask and replaced with the distillation apparatus. The pressure in the system is reduced to 50 mm Hg and the toluene and SBA are distilled off. About 178 g of CBE is recovered, assaying 94-96%, for a yield of about 95% (based on CBA charged).

CYCLIZATION

Example 4

To a 1000 ml round-bottomed flask, 90 gm (2.25 mole) NaOH, 200 gm wet methylene chloride, and 6 gm tributylmethylammonium chloride (70%) is charged. The mixture is heated to a slow reflux (40° C.) and 282 gm (1.5 mole) 95% sec-butyl-4-chlorobutyrate is added dropwise over one hour. The mixture now refluxes at about 55° C. Reflux is continued until conversion of the 4-chlorobutyrate ester is complete (about one hour), as determined by g/c.

The batch is cooled to 25° C. and 400 ml water are added. The layers are separated and the water layer is extracted twice with 50 ml methylene chloride each time. The organic layers are combined and solvent is fractionally distilled until all the methylene chloride is removed. Distillation is continued until the overhead temperature reaches 130° C. The contents of the flask are cooled. About 202 grams of sec-butylcyclopropane-car-boxylate is obtained, about 98% assay or 93% yield based on the starting ester.

Example 5

To a 1000 ml round-bottomed flask 90 gm (2.25 mole) NaOH, 200 gm methylene chloride, 6 gm tributylmethylammonium chloride (70%) and 282 gm (1.5 moles) 95% sec-butyl-4-chlorobutyrate are charged. The mixture is agitated and the temperature of the mixture is controlled at 30° C. with a water bath. These conditions are continued until conversion is complete (about six hours). When conversion is complete, the product is worked up as in example 4. Yield: About 213 gm 98% sec-butyl-cyclopropanecarboxylate, or 98% yield.

Example 6

The procedure of example 5 is followed, except methyl t-butyl ether is used instead of methylene chloride. The reaction time is about four hours and the yield is 97%.

Example 7

To a one liter flask equipped with mechanical stirrer, thermometer, condenser and dropping funnel is charged 60 g of (1.5 moles) caustic beads, 3 g of tributylmethylammonium chloride and 178 g of dichloromethane. This mixture is heated to reflux (40° C.), and 178.6 g (1.0 mole) of sec-butyl chlorobutyrate is added dropwise at a rate such that reflux does not become excessive. The batch is then held at reflux until analysis by gas chromatography shows the reaction to be complete (~2 hours). The batch is then cooled, 250 g of water is added, and the layers are separated. The aqueous layer is extracted twice with 50 ml portions of dichloromethane, and the organic layers are combined. Removal of the solvent affords 139 g of product assaying 96.6% sec-butyl cyclopropanecarboxylate, a 94.6% yield.

Example 8—CPE Pilot Plant Example

To a 300 gallon SS reactor is charged 200 lbs. (5 moles) sodium hydroxide beads, 600 lbs. methylene chloride, 18 lbs. tributylmethylammonium chloride, and 0.5 gallon water. The mixture is heated to 30° C. with agitation. Sec-butyl 4-chlorobutyrate (CBE) is added at 3-4 lbs. per minute until a total of 600 lbs. (3.36 moles) is added, controlling the reaction temperature between 30°-35° C. by using −10° C. brine on the reactor. The batch is stirred at this temperature until the conversion of CBE is >99.5%. This requires about 7 hours from the time the CBE addition is begun.

The batch is then cooled to 20° C., and 120 gallons of water added. The mixture is stirred 15 minutes, and the layers allowed to separate. The water layer, containing the by-product NaCl, is removed as the bottom layer.

The organic layer is washed with an additional 50 gallons of water as before. The organic layer (this time the bottom layer) is separated and transferred to a 300 gallon glass lined reactor equipped with a fractionating still.

The water layers are combined in the stainless steel reactor and washed once with 225 lbs. methylene chloride. The organic layer (bottom) is transferred to the distillation vessel, and the water layer is discarded.

The methylene chloride is distilled at about 40° C. overhead until the pot temperature reaches 130° C. The distilled methylene chloride is drummed out, and the system put under vacuum (25"). An intermediate cut is distilled to an overhead temperature of 80° C. and a pot temperature of 103° C. The batch is then cooled and drummed to yield 457 lbs. CPE, assaying 97.2% or 93.0% yield. A further 24 lbs. of CPE is in the distilled solvent cuts, giving an overall yield of 98.1% based on CBE when these cuts are recycled.

AMMONOLYSIS

Example 9

102.5 g of 96.6% assay methyl cyclopropanecarboxylate (MCPC) (0.99 g mole) is charged to a 1 liter Parr pressure reactor. Also charged are: 250 ml mixed xylenes, 50 g dry ethylene glycol and 0.2 g mole sodium ethylene glycoxide dissolved in methanol. The Parr reactor is sealed and agitating is started. The reactor is pressured to 100 psig with ammonia and then heated to 100° C. The maximum pressure is 230 psig. The reactor is held at 100° C. for 3 hours and 10 minutes, then it is cooled to 25° C. The reactor is opened and the reaction mass is dissolved in methanol to yield 682.4 g of solution. This solution analyzes 11.2% CPAM and 0.3% MCPC for a 98% conversion and a 91% CPAM yield.

Example 10

188.1 g of 91.5% assay isopropyl cyclopropanecarboxylate (IpCPC, 2.34 g moles), 300 ml xylenes, 75 g dry ethylene glycol and 0.3 g moles sodium ethylene glycoxide (dissolved in methanol) are charged to a 1 liter Parr pressure reactor. The reactor is sealed and pressured with ammonia to 100 psig, while agitating. The reaction mass is heated to 100° C. and held 5 hours; maximum pressure is 232 psig. The reactor is cooled and the contents are dissolved in methanol to yield 903.2 g of solution. Analytical results indicate a 98% conversion of esters and a 92.7% CPAM yield.

Example 11

To a 2 liter Parr pressure reactor are charged: 360.3 g of 98.6% 2-butyl cyclopropanecarboxylate (CPE 2.5 g moles) and 188 g of sodium ethylene glycoxide/ethylene glycol solution (0.5 mole of alkoxide). The reactor is sealed, agitated and 55.3 g ammonia is charged (3.25 g mole). The temperature rises to 43° C. at 85 psig. The reactor is then heated to 100° C. and held 5 hours. The maximum pressure is 127 psig. The final pressure is 60 psig. The reactor is cooled in ice and the reaction mass is transferred to a 5 neck, 3 liter, round bottom flask. This flask is connected as an agitated still pot for a 20 stage Oldershaw column. Along with some 2-butanol rinse, 25 g of 98% $H_2SO_4$, 10 g of water, 10 g $NaHCO_3$ and 100 ml p-cymene are charged to the still pot. The 2-butanol is then distilled at 50 mm Hg total pressure until 2 phase glycol/cymene distillate is obtained overhead (75 ml alcohol). Using a decanter containing another 125 ml cymene, the ethylene glycol is azeotropically removed at 50 mm Hg pressure; cymene goes back to the still. When 167.5 g glycol has been removed, the distillation is stopped and 1400 g water is added to the still to dissolve the CPAM. The cymene is then steam stripped and decanted at 150 mm Hg pressure. The cooled water layer weighs 1879.8 g and it assays 10.5% CPAM for a 92.8% yield. CPAM in the recovered glycol brings the total CPAM yield to 94.6%.

Example 12

To the 2 l. reactor are charged 300 g of 94.8% CPE (2.0 g moles) and 1.0 g mole sodium ethylene glycoxide (84 g) dissolved in 292 g ethylene glycol. The reactor is sealed and agitation is started. 52 g of ammonia is charged (3.05 g mole). The reactor is heated to 100° C. and held 3 hours. The reaction mass is pressured into an Erlenmeyer flask, padded with dry $N_2$, and then cooled to 23° C., forming a CPAM slurry. The slurry is filtered and the filter cake is washed with 50 g of cold 2-butanol. The filter cake is dried to provide a 45.2% CPAM yield. The filtrate is distilled to remove 2-butanol at 30 mm Hg total pressure until the pot temperature reaches 100° C. The still bottoms are then charged to the 2 l.Parr reactor with 300 g more ester and the reaction and workup is repeated as above. For the seven recycle batches, the following yields are obtained: 87.5%, 94.2%, 97.7%, 91.1%, 88%, 90.4% and 50.7%.

Batch eight is returned to the reactor with 75 g fresh glycoxide solution in glycol (no ester added), and a final batch is made. The CPAM produced brings the batch 8 total yield to 106.5%. Filtrate from batch 8 is recovered via the cymene distillation (example 3) to yield another 1.0 g mole of CPAM. The cumulative CPAM "in-hand" yield over the 8 batches is 93.9%, based upon CPE.

Example 13

Sodium glyceroxide is prepared by vacuum stripping the water from a boiling mixture of 103 g glycerol (1.12 g mole). 40 g solid caustic (1.0 g mole) and 300 ml xylenes. The strip takes 1 hour. 500 g methanol is added to attempt to dissolve the sodium glyceroxide, but a slurry results.

To the 1 liter Parr pressure reactor is charged 300 ml xylenes, 100 g of distilled methyl cyclopropanecarboxylate (MCPC, 1.0 g mole), and 84 g of the sodium glyceroxide slurry (0.2 g mole). The reactor is sealed and pressured to 100 psig with ammonia. The reactor is heated to 100° C. and held 7 hours. A G.C. scan shows that much ester remains. The system is shutdown overnight. The next morning, 10 g more glycerol is charged to the reactor. The reactor is sealed and pressured to 100 psig with ammonia. Heatup to 100° produces about 300 psig pressure. After 5 hours, no ester is observed in a G.C. scan so the system is shutdown, cooled and the reaction mass is dissolved in methanol to yield 755.2 g of solution. Analysis is 9.7% CPAM and no ester is detected. The yield of CPAM is 86.1%.

Example 14

To a 2 liter, agitated, round bottom flask is charged 651 g (5 g moles) 2-ethyl-1-hexanol, 150 ml xylenes and 49 g (1.2 g moles) solid caustic. The mixture is heated to reflux at about 170° C. pot temperature through a packed column. After 2 hours, about 18 g of water has collected in an overhead decanter. The xylenes are allowed to distill off, raising the pot temperature to 180° C. and another 2.5 g of water comes out (1.14 g mole total). The reaction mass is cooled to 100° C. and 152.6 g of 89.5% methyl chlorobutyrate is charged over 3 hours. A G.C. scan reveals one product peak of 2-ethyl-1-hexyl cyclopropanecarboxylate. The entire reaction mass is charged to a 2 liter Parr pressure reactor along with 0.2 g mole (17 g) sodium ethylene glycoxide in 50 g glycol. The reactor is sealed, agitated and pressured to 100 psig with ammonia. The reaction mass is heated to 100° C. and held 2 hours. A G.C. run indicated ester remains. After 2 hours more, the ester level remains unchanged; the reaction has reached equilibrium (note that the reactor contains 5 g moles of alcohol). The reactor is cooled and the reaction mass is dissolved in methanol to yield 1292.4 g of solution. Analysis shows 5.4% CPAM, 0.1% MCPC and about 5 mole % of the 2-ethyl-1-hexyl ester remains. Yield is 82% CPAM on a conversion of about 94%.

Example 15—Preparation of Catalyst

To a 2 liter, agitated, round bottom flask are charged 1860 g of ethylene glycol and 200 g of solid sodium hydroxide. The mixture is started agitating and placed under vacuum at 30 mm Hg total pressure. The mixture is heated and water is distilled over at 35° C. overhead temperature through a 20 stage Oldershaw column. The column is set for about a 1:1 reflux ratio.

Distillation continues until all water is removed and the overhead temperature reaches the glycol boiling point. A total of 120 ml of distillate is collected. The sodium ethylene glycoxide is cooled and bottled for use as a catalyst at 0.1 g-mole/38.8 g solution.

Example 16—Pilot Plant Scale—CPAM

To a 50 gallon pilot plant reactor is charged 80 lbs. of sodium ethylene glycoxide/ethylene glycol solution containing 0.2 lb. moles of sodium ethylene glycoxide. To the reactor is also charged 145 lbs. of 98.7% CPE or 1 lb. mole. The reactor is sealed and heated to about 90° C. under agitation. To the reactor is charged 22 lbs. of anhydrous ammonia, taking about 1 hour to complete the charge. During the ammonia charge, the temperature rises to 100° C., where it is maintained. The reaction mass is held 3 hours at 100° C., to complete reaction, and then cooling is applied to reduce the reaction mass temperature to 0° C. Product CPAM precipitates and it is isolated by filtration. Filtrate is kept anhydrous under a dry nitrogen pad. To the reactor is charged 50 lbs. 2-butanol, which is chilled to 0° C. and applied to the CPAM filter cake, as a wash. The CPAM is dried in a tray dryer at 50° C. under vacuum with a nitrogen purge.

The filtrate and 2-butanol wash are returned to the reactor. Ammonia and 2-butanol are removed by vacuum distillation, at 50 mm Hg pressure, until the reactor temperature reaches 100° C. Fresh CPE is charged to the recycled catalyst mixture and the reaction is repeated as above.

This catalyst recycle process is repeated through 5 batches with the following in-hand yields, respectively: 79%, 93.1%, 93.5%, 98.5% and 97.2%. The average in-hand yield is 92.3% on an overall CPE conversion of 99.4%. An additional 3.6% CPAM yield remains in the final filtrate, for a total CPAM yield of 95.9%.

Example 17—Cyclopropylamine Preparation

To a 2 liter four-neck flask equipped with a dropping funnel, thermometer, ice bath, vent and agitator is charged 170.2 grams cyclopropane carboxamide (100% assay) and 500 grams tap water. The mixture is cooled to 5° C. with agitation.

To the mixture is charged 805 grams of bleach (18.5% NaOCl, 2 gram moles) containing 1.8% NaOH, maintaining 0°–5° C. with cooling. The reaction mass is stirred for one hour at 0°–5° C. after the addition of bleach.

A continuous feed distillation column, consisting of a six inch long, 1 inch ID packed stripper, a feed point above the stripper, a 24 inch packed column above the feed point, and overhead condenser and reflux splitter, with a 2 liter flask and heating mantle containing 100 grams of water as a reboiler, is heated until full reflux is obtained.

The reaction mixture is fed into the feed point concurrently with 50% NaOH solution, the two feeds controlled to 2.0 to 2.25 gram moles of caustic per gram mole of reaction product. The NaOH/reaction mixture is heated by the refluxing water, exothermically decomposing ty cyclopropylamine, salt, and sodium carbonate. The cyclopropylamine is continuously distilled overhead while the salt solution accumulates in the reboiler.

A 94.1% yield of cyclopropylamine was contained in the distillate.

What is claimed is:

1. In the process for preparing cyclopropylamine from gamma-butyrolactone comprising the steps of (1) cleaving the gamma-butyrolactone ring with a hydrohalide in the presence of a catalyst to form 4-chlorobutyric acid; (2) esterifying said 4-chlorobutyric acid with an aliphatic alcohol to form the 4-chlorobutyrate ester; (3) cyclizing the 4-chlorobutyrate ester to the cyclopropanecarboxylate ester; (4) converting the ester to cyclopropanecarboxamide; (5) converting cyclopropanecarboxamide to cyclopropylamine by a Hofmann reaction; and recovering the purified cyclopropyl-amine; the improvements wherein
   (1) the hydrohalide cleaving is promoted by the presence of an aqueous solution of sulfuric acid at a temperature in the range 65°–75° C. and 0–300 psig;
   (2) esterifying the thus formed 4-chlorobutyric acid with a secondary or tertiary aliphatic alcohol to form a sterically hindered 4-chlorobutyrate ester;
   (3) cyclizing said hindered 4-chlorobutyrate ester to form the hindered cyclopropane-secondary or tertiary carboxylate ester in the presence of a solid alkali metal hydroxide and a phase transfer catalyst in a water-immiscible solvent at temperatures from about 20° to 60° C.;
   (4) converting the cyclopropanecarboxylate-secondary or tertiary alcohol ester to the cyclopropanecarboxamide by reacting it with ammonia at a temperature of 25°–150° C. in the presence of a catalyst comprising an alkali metal salt of a polyhydric alcohol having at least two hydroxyl groups located on adjacent carbon atoms; and
   (5) then converting the resulting cyclopropanecarboxamide to cyclopropylamine by a modified Hofmann reaction with alkaline hypohalite and aqueous alkaline hydroxide and then recovering said cyclopropylamine product by feeding the chlorinated intermediate with excess caustic into a continuous distillation column.

2. In the process according to claim 1 which includes ring cleavage of gamma-butyrolactone by a hydrohalide, the specific improvement which comprises the step of performing the ring cleavage by hydrogen chloride in the presence of a catalytic amount of sulfuric acid and water in a pressurized vessel at a temperature in the range 65°–75° C.

3. In the process according to claim 2 wherein the proportions of sulfuric acid to water is in the range 1:1 to 1:5.

4. In the process according to claim 3 wherein the proportion of sulfuric acid to water is in the range 1:2 to 1:3 and is present in an amount equal to 5 to 10 wt.% of the reaction mixture.

5. In the process according to claim 1 wherein 4-chlorobutyric acid is esterified to form the 4-chlorobutyrate ester, the improvement wherein said 4-chlorobutyric acid is esterified with an alcohol selected from the group consisting of secondary and tertiary alcohols of eight or less carbon atoms to form said hindered esters.

6. In the process according to claim 1 wherein the 4-chlorobutyrate ester of the formula

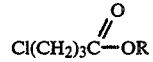

is cyclized to form the cyclopropanecarboxylate ester of the formula

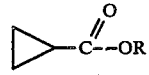

the improvement wherein O—R is an alkanol residue of a secondary or tertiary alcohol of 8 or less carbon atoms and said cyclization step includes contacting said 4-chlorobutyrate ester of said secondary or tertiary alcohol with a solid alkali metal hydroxide in the presence of a quaternary ammonium salt phase transfer catalyst and a water-immiscible solvent for said carboxylates, within the temperature range 20° to 60° C.

7. In the process according to claim 6 wherein said water-immiscible solvent is selected from among liquid aliphatic or aromatic hydrocarbons, chlorinated hydrocarbons, and aliphatic ethers.

8. In the process according to claim 6 wherein said solid alkali metal hydroxide consists of sodium hydroxide.

9. In the process according to claim 1 wherein said hindered secondary or tertiary ester of cyclopropanecarboxylic acid is amidated to cyclopropanecarboxamide by reacting said ester with ammonia in the presence of said catalyst, said reaction being conducted at a temperature in the range 85°–115° C. at autogenous pressures when said catalyst is sodium ethylene glycoxide.

10. The process according to claim 9 wherein said sodium ethylene glycoxide catalyst is prepared by adding sodium hydroxide to an excess of ethylene glycol and then stripping all the water from said reaction mixture.

11. The process according to claim 1 wherein said cleaved γ-butyrolactone is esterified to form a hindered 4-chlorobutyrate ester, which is then cyclized to form the hindered cyclopropanecarboxylate ester, which is substantially converted to cyclopropanecarboxamide by ammonia in the presence of a catalyst comprising sodium ethylene glycoxide, and then, by a Hofmann reaction, preparing cyclopropylamine.

12. The process according to claim 11 wherein said cyclopropylamine is recovered by feeding the chlorinated intermediate with excess caustic into a continuous distillation column.

13. The process of preparing 4-chlorobutyric acid from γ-butyrolactone which comprises reacting γ-butyrolactone with hydrogen chloride in the presence of a catalytic amount of a 20 to 50% aqueous solution of sulfuric acid, said amount comprising 5-10 wt.% of the reaction mass.

14. The process of preparing cyclopropanecarboxylic hindered esters which comprises the step of reacting a hindered 4-chlorobutyrate ester of the formula

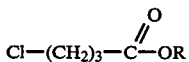

where —OR is the alkanol residue of a secondary or tertiary alcohol of eight or less carbon atoms with solid alkali metal hydroxides in the presence of a water-immiscible solvent and a quaternary ammonium phase transfer catalyst and recovering said cyclopropane carboxylate esters.

* * * * *